(12) United States Patent
Aljindan et al.

(10) Patent No.: US 10,670,544 B2
(45) Date of Patent: Jun. 2, 2020

(54) IMPEDANCE-BASED FLOWLINE WATER CUT MEASUREMENT SYSTEM

(71) Applicant: Saudi Arabian Oil Company, Dhahran (SA)

(72) Inventors: Jana Mohammed Aljindan, Dhahran (SA); Mohamed Nabil Noui-Mehidi, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 45 days.

(21) Appl. No.: 16/102,192

(22) Filed: Aug. 13, 2018

(65) Prior Publication Data

US 2020/0049634 A1    Feb. 13, 2020

(51) Int. Cl.
*G01N 22/04* (2006.01)
*G01F 1/74* (2006.01)
*G01N 33/18* (2006.01)

(52) U.S. Cl.
CPC ............... *G01N 22/04* (2013.01); *G01F 1/74* (2013.01); *G01N 33/1833* (2013.01)

(58) Field of Classification Search
CPC .. G01N 22/04; G01N 33/1833; G01N 17/008; G01F 1/74; G01F 1/56; G01R 27/22
See application file for complete search history.

(56) References Cited

U.S. PATENT DOCUMENTS

| 5,070,725 | A | 12/1991 | Cox et al. |
| 5,095,758 | A | 3/1992 | Cox et al. |
| 6,320,156 | B1* | 11/2001 | Yamaguchi ............. H05H 1/34 |
| 6,467,358 | B1* | 10/2002 | Nishi ..................... G01F 1/363 |
| | | | 73/861.04 |

(Continued)

FOREIGN PATENT DOCUMENTS

| WO | 200046133 | 8/2000 |
| WO | 2008003365 | 1/2008 |

OTHER PUBLICATIONS

Kyle et al., "Bioelectrical impedance analysis—part 1: review of principles and methods," Clinical Nutrition, Oct. 2004, 18 pages.

(Continued)

*Primary Examiner* — Christopher P McAndrew
*Assistant Examiner* — Zannatul Ferdous
(74) *Attorney, Agent, or Firm* — Fish & Richardson P.C.

(57) ABSTRACT

A water cut measurement tool includes an elongated tubular section configured to flow a multiphase fluid including water and hydrocarbons. The elongated tubular section includes two portions. A first portion has a first diameter. A second portion is axially coupled to the first portion and has a second diameter less than the first diameter. The second portion can receive the multiphase fluid from the first portion. A first electrode is attached to an inner wall of the second portion. A second electrode is attached to the inner wall of the second portion and is positioned diametrically opposite to the first electrode. The two electrodes are configured to measure an impedance of the multiphase fluid flowed through the second portion responsive to a current flowed from the first electrode to the second electrode, and provide the impedance as an output.

20 Claims, 3 Drawing Sheets

(56) References Cited

U.S. PATENT DOCUMENTS

| | | | | |
|---|---|---|---|---|
| 6,655,221 | B1 * | 12/2003 | Aspelund | G01F 1/363 |
| | | | | 73/861.04 |
| 8,072,226 | B2 * | 12/2011 | Park | G01N 27/4146 |
| | | | | 324/537 |
| 2003/0074982 | A1 | 4/2003 | Spielman | |
| 2003/0141882 | A1 * | 7/2003 | Zou | G01N 27/226 |
| | | | | 324/698 |
| 2011/0259120 | A1 | 10/2011 | Thonstad | |
| 2011/0267074 | A1 | 11/2011 | Xie et al. | |
| 2013/0110411 | A1 | 5/2013 | Black et al. | |
| 2014/0260659 | A1 * | 9/2014 | Sheila-Vadde | G01F 1/74 |
| | | | | 73/861.04 |
| 2015/0293056 | A1 * | 10/2015 | Kelly | G01N 27/44717 |
| | | | | 204/549 |
| 2016/0076925 | A1 * | 3/2016 | Chen | G01F 1/44 |
| | | | | 702/49 |
| 2016/0284979 | A1 * | 9/2016 | Fukui | H01L 41/0815 |
| 2017/0090060 | A1 * | 3/2017 | Donderici | E21B 47/0005 |
| 2019/0002722 | A1 * | 1/2019 | May | C09D 11/36 |

OTHER PUBLICATIONS

Ismail et al., "Microcontroller Based Automated Body Mass Index (BMI) Calculator with LCD Display," 2nd International Conference on Electrical, Electronics and Civil Engineering (ICEECE'2012), Apr. 28-29, 2012, 3 pages.

International Search Report and Written Opinion issued in International Application No. PCT/US2019/045417 dated Oct. 23, 2019, 15 pages.

* cited by examiner

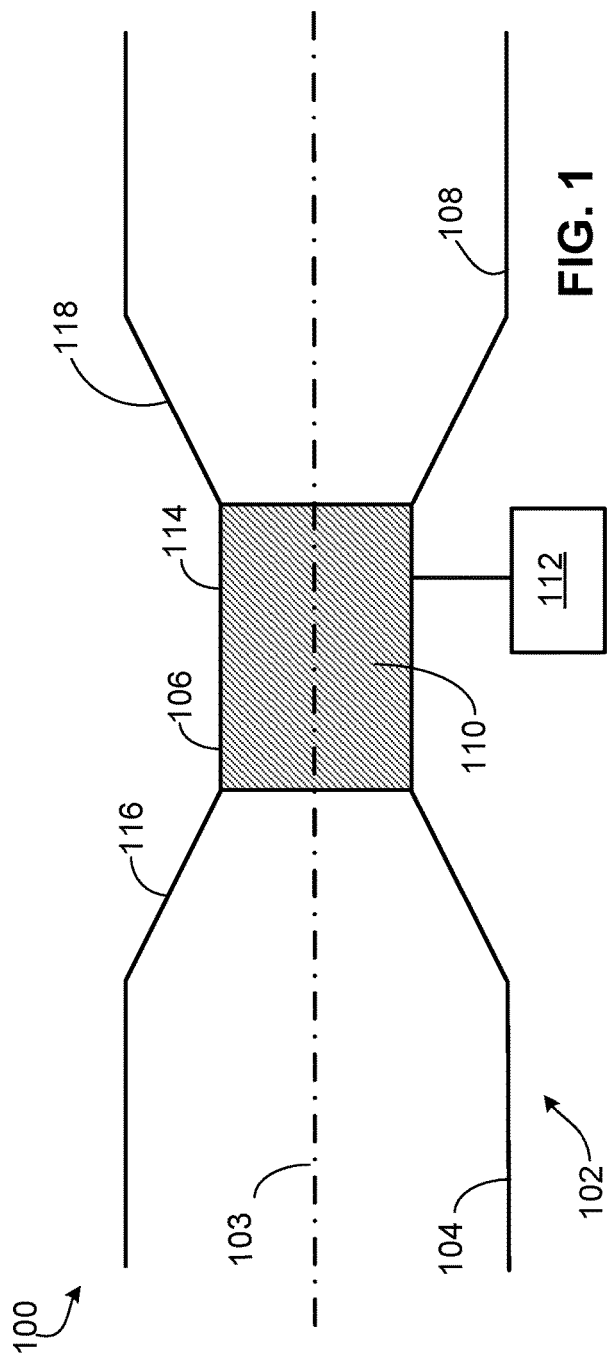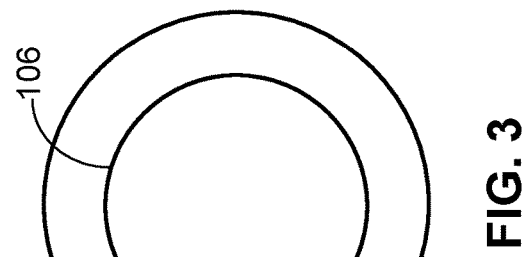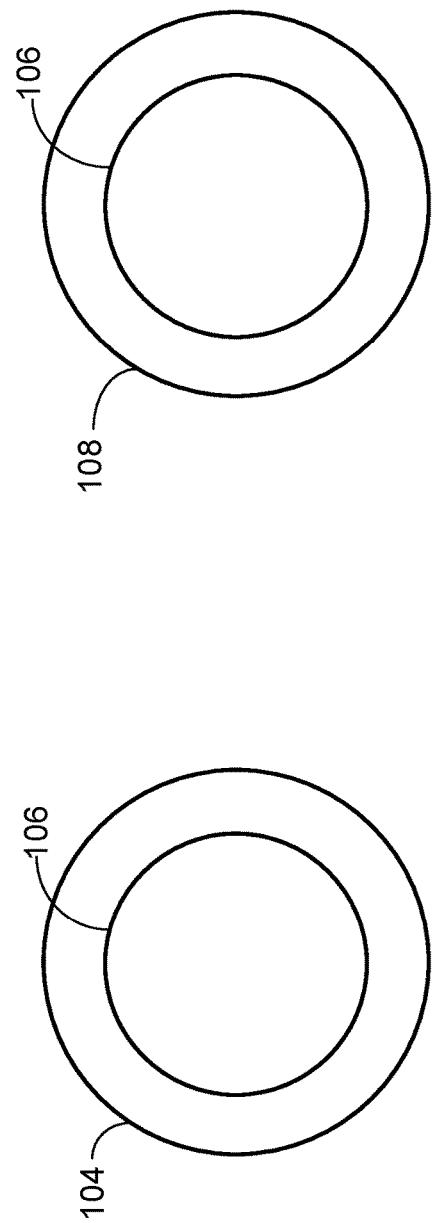

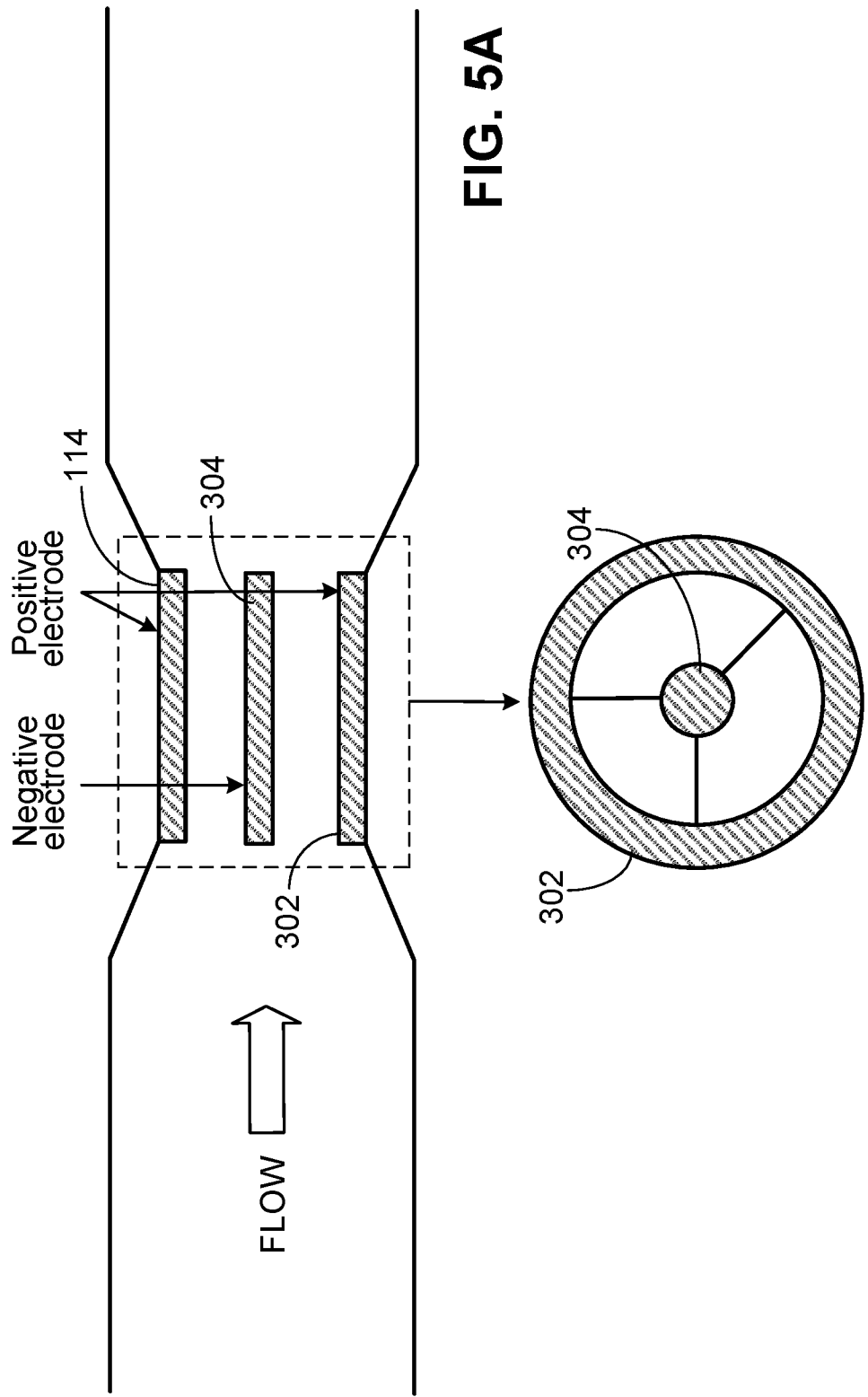

IMPEDANCE-BASED FLOWLINE WATER CUT MEASUREMENT SYSTEM

TECHNICAL FIELD

This specification relates to flow measurement tools, for example, tools that can measure parameters of multiphase fluid flow.

BACKGROUND

Hydrocarbons produced from hydrocarbon reservoirs are multi-phase fluids that include hydrocarbons, water, gas or combinations of them. Water cut is defined as a ratio of water produced to a total volume of hydrocarbons produced. Water cut is one measure of an efficiency of a producing well.

SUMMARY

This specification describes technologies relating to impedance-based water cut measurement systems.

Certain aspects of the subject matter described here can be implemented as a water cut measurement system. The system includes an elongated tubular section configured to flow a multiphase fluid including water and hydrocarbons. The elongated tubular section includes a first portion, a second portion and a third portion. The first portion has a first diameter. The second portion is axially coupled to the first portion and has a second diameter less than the first diameter. The third portion is axially coupled to the second portion and has a third diameter greater than the second diameter. The measurement system includes an electrode sub-system positioned in the second portion of the elongated tubular section and that includes two electrodes configured to flow a current. The measurement system includes a controller coupled to the electrode sub-system. The controller is configured to determine a ratio of hydrocarbons to water in the multiphase fluid flowed through the elongated tubular section based on an impedance measured by the electrode sub-system responsive to the current flowed through the electrode sub-system.

In some aspects combinable with any of the other aspects disclosed here, each of the first portion, the second portion and the third portion has a circular cross-section.

In some aspects combinable with any of the other aspects disclosed here, the second portion includes an axial portion that is parallel to a longitudinal axis of the elongated tubular portion. The electrode sub-system is attached to an inner wall of the axial portion.

In some aspects combinable with any of the other aspects disclosed here, the first electrode and the second electrode are attached to diametrically opposite regions of the inner wall of the axial portion.

In some aspects combinable with any of the other aspects disclosed here, an outer surface of each of the first electrode and the second electrode has a shape that is identical to a shape of the inner wall of the axial portion.

In some aspects combinable with any of the other aspects disclosed here, an inner surface of each of the first electrode and the second electrode has a tapered edge.

In some aspects combinable with any of the other aspects disclosed here, a tapered edge of the first electrode and a tapered edge of the second electrode are aligned on a plane perpendicular to a longitudinal cross-section of the elongated tubular section.

In some aspects combinable with any of the other aspects disclosed here, ends of the first electrode and ends of the second electrode are separated by a radial gap.

In some aspects combinable with any of the other aspects disclosed here, the first electrode is formed as an annular disc. An outer surface of the annular disc contacts the inner wall of the axial portion.

In some aspects combinable with any of the other aspects disclosed here, the second electrode is formed as a solid tube positioned concentrically within the annular disc.

In some aspects combinable with any of the other aspects disclosed here, a thickness of the annular disc is based on the current flowed through the electrode sub-system.

In some aspects combinable with any of the other aspects disclosed here, the first diameter is equal to the third diameter.

In some aspects combinable with any of the other aspects disclosed here, the second portion includes a first conical tubular portion that couples the first portion to the second portion, and a second conical tubular portion that couples the third portion to the second portion.

Certain aspects of the disclosure described here can be implemented as a water cut measurement tool. The tool includes an elongated tubular section configured to flow a multiphase fluid including water and hydrocarbons. The elongated tubular section includes two portions. A first portion has a first diameter. A second portion is axially coupled to the first portion and has a second diameter less than the first diameter. The second portion can receive the multiphase fluid from the first portion. A first electrode is attached to an inner wall of the second portion. A second electrode is attached to the inner wall of the second portion and is positioned diametrically opposite to the first electrode. The two electrodes are configured to measure an impedance of the multiphase fluid flowed through the second portion responsive to a current flowed from the first electrode to the second electrode, and provide the impedance as an output.

In some aspects combinable with any of the other aspects disclosed here, the tool includes a third portion axially coupled to the second portion and having a third diameter greater than the second diameter.

In some aspects combinable with any of the other aspects disclosed here, the second portion includes an axial portion that is parallel to a longitudinal axis of the elongated tubular portion. The first electrode and the second electrode are attached to an inner wall of the axial portion.

In some aspects combinable with any of the other aspects disclosed here, the first electrode is formed as an annular disc. An outer surface of the annular disc contacts the inner wall of the axial portion. The second electrode is formed as a solid tube positioned concentrically within the annular disc.

The details of one or more implementations of the subject matter described in this specification are set forth in the accompanying drawings and the description that follows. Other features, aspects, and advantages of the subject matter will become apparent from the description, the drawings, and the claims.

BRIEF DESCRIPTION OF THE DRAWINGS

FIG. 1 is a schematic of a water cut measurement system.
FIG. 2 is a schematic of a cross-sectional view of the water cut measurement system of FIG. 1.
FIG. 3 is a schematic of a cross-sectional view of the water cut measurement system of FIG. 1.

FIGS. 5A and 5B are schematics of a second implementation of an electrode sub-system in the water cut measurement system of FIG. 1.

Like reference numbers and designations in the various drawings indicate like elements.

DETAILED DESCRIPTION

Figure 4A:
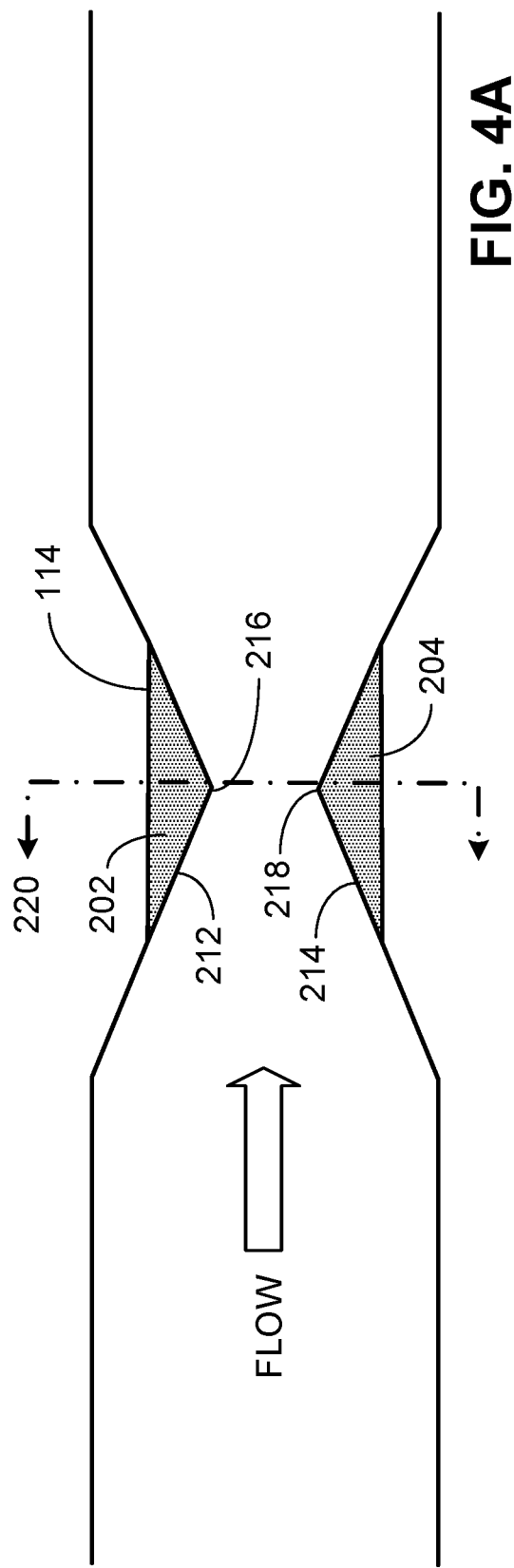
FIGS. 4A and 4B are schematics of a first implementation of an electrode sub-system in the water cut measurement system of FIG. 1.

This specification describes methods and systems for oil content measurements in a water-rich flow stream. In some implementations, the measurement system includes a pipe that has a section with a smaller diameter compared to the rest of the pipe. Positive and negative electrodes are positioned in this reduced-diameter section. Electrical current is applied between the electrodes as a multiphase fluid that includes water and oil flows through the pipe. Impedance between the two electrodes and across the cross-section of the reduced-diameter section is measured. The impedance measurement is used to determine an amount of oil in the water stream. Measuring the amount of oil in water (or water in oil) allows evaluating contents of any polluting oil phase present in a water-rich stream.

The water cut measurement technique described in certain implementations of this specification is based on a difference in flow of alternating current through different fluids flowing through a flowline. For example, water is a better conductor of current compared to oil. Thus, when water flows between an anode and a cathode, the impedance to flow of current from the cathode to the anode through the water is minimal. Conversely, when oil flows between the anode and the cathode, the impedance to flow of current from the cathode to the anode through the oil is greater than that through the water. When a multiphase fluid which includes oil and water flows between the anode and the cathode, the impedance to flow of current from the cathode to the anode at any given time instant varies based on the amounts of oil and water in the multiphase fluid at that time instant. For example, if the impedance responsive to flow of water alone is assumed to be zero and the impedance responsive to flow of oil alone is assumed to be one, then the impedance responsive to flow of a mixture of oil and water can fall between zero and one.

The measurement system described in this specification can be implemented to measure quantities of component fluids other than oil and water. For example, as long as a multiphase fluid includes components, each of which exhibits a different impedance to flow of current, the measurement system can be used to determine amounts of individual components. To do so, an impedance of zero can be associated with a fluid component with greater conductance and an impedance of one can be associated with a fluid component of comparatively lesser conductance. Based on a measured impedance value (between zero and one), the quantity of each fluid component in the multiphase fluid can be determined. In this specification, the measurement system is described with reference to a multiphase fluid that includes oil or gas mixed with water.

FIG. 1 is a schematic of a water cut measurement system 100. The system 100 includes an elongated tubular section 102 that can flow a multiphase fluid. For example, the fluid can include a hydrocarbon that includes hydrocarbons (such as oil), water, gas or combinations of them. The hydrocarbon can have been produced from a wellbore formed in a hydrocarbon reservoir. The system 100 can be implemented at the wellbore (for example, at a surface of the wellbore) or as part of a flowline that carries the produced hydrocarbon from the wellbore to a different location. The system 100 includes three portions—a first portion 104 having a first diameter, a second portion 106 axially coupled to the first portion 104 and having a second diameter and a third portion 108 axially coupled to the second portion 108. In some implementations, each of the first portion 104 and the third portion 108 can include fluid couplings to couple the system 100 to a flowline to receive the multiphase fluid into and flow the multiphase fluid out of the system 100.

FIG. 2 is a schematic of a cross-sectional view of the water cut measurement system 100 of FIG. 1. FIG. 3 is a schematic of a cross-sectional view of the water cut measurement system 100 of FIG. 1. As shown in FIG. 2, a diameter of the second portion 106 is smaller than that of the first portion 104. As shown in FIG. 3, a diameter of third portion 108 is greater than that of the second portion 106. In some implementations, the diameter of the first portion 104 and the third portion 106 can be the same, while in other implementations, the diameters can be different. FIGS. 2 and 3 show that the three portions have circular cross-sections. In some implementations, the cross-sectional shapes can be different from circular.

In some implementations, an end of the first portion 104 can be connected to an end of the second portion 106 by a conical tubular portion 116. As multiphase fluid flows from the first portion 104 to the second portion 106, the conical tubular portion 116 funnels the multiphase fluid into the second portion 106. In this sense, the conical tubular portion 116 can function as a Venturi. In some implementations, an end of the second portion 106 can be connected to an end of the third portion 108 by a conical tubular portion 118. As multiphase fluid flows from the second portion 106 to the third portion 108, an increase in the cross-sectional area due to the conical tubular portion 118 causes the portion 118 to function as a diffuser.

The measurement system 100 includes an electrode sub-system 110 positioned in the second portion 106 of the elongated tubular section. The electrode sub-system 110 includes two electrodes through which current, for example, alternating current (AC) can flow. As described in detail later, the two electrodes can be positioned in the second tubular portion 106 in the flow path of the multiphase fluid. In some implementations, the second tubular portion 106 includes an axial portion 114 that is parallel to a longitudinal axis 103 of the elongated tubular portion 102. The electrode sub-system 110 is attached to an inner wall of the axial portion 114. Because the inner diameter of the second tubular portion 104 is less than the first tubular portion 102, attaching the electrodes to the inner wall of the second tubular portion 104 decreases a distance between the two electrodes. In turn, the distance by which the current flows between the electrodes decreases resulting in an increased sensitivity of the measurement system 100 or an ability of the system to sense impedance responsive to low levels of current (for example, in the range of 0.1 milliAmpere (mA) to 0.5 mA).

When the multiphase fluid contacts the two electrodes, an electrical circuit is completed to flow alternating current from one of the two electrodes to the other. An impedance to the flow of the alternating current depends on the fluid flowing between the two electrodes. For example, water offers less impedance (for example, zero impedance), oil offers comparatively greater impedance (for example, a normalized impedance of one) and a mixture of the two offers an intermediate impedance (for example, between zero and one).

The measurement system 100 includes a controller 112 coupled to the electrode sub-system 110. In some implementations, the controller 112 can be implemented as a computer system including a computer-readable medium storing instructions executable by one or more processors to perform the operations described here. In some implementations, the controller 112 can be implemented as software, firmware, hardware, processing circuitry or combinations of them.

The controller 112 can determine a ratio of hydrocarbons to water in the multiphase fluid flowed through the elongated tubular section 102 based on an impedance measured by the electrode sub-system responsive to the current flowed through the electrode sub-system 110. In some implementations, the controller 112 and the electrode sub-system 110 can be connected to a power source, which together with the electrode sub-system 110 and the flowing multiphase fluid forms an electrical circuit through which alternating current can flow. In some implementations, a constant current (for example, in a range between 0.1 mA to 0.5 mA) can be flowed between the electrodes in the electrode sub-system 110 as the multiphase fluid flows through the second tubular portion 104. A voltage across the electrode sub-system 110 can be measured. The voltage will be a function of an impedance of the fluid flowing through the second tubular portion 104. By measuring the voltage, the impedance can be determined, and the water cut can be determined from the impedance.

In the example in which the multiphase fluid is a mixture of oil and water or gas and water, water is considered as the only fluid through the second tubular portion 104 with electrical conductivity. When the current passes through the tube, the impedance of the water is measured from which the volume of water is calculated. For example, the volume (V) of the water in the second tubular portion 104 can be measured by multiplying the area of the tube (A) by the length of the tube (V). The impedance is proportional to the length and inversely proportional to the area. Therefore, the impedance (Z) due to water in the second tubular portion 104 can be related to the volume of water in the second tubular portion 104 using Equation 1.

$$Z = Q \times (L^2)/V \qquad \text{(Eq. 1)}$$

In Eq. 1, Q is the specific resistivity of the water, L is the length of the second tubular portion 104 and V is the volume of water in the second tubular portion 104. Having determined impedance (Z) (that is, voltage (V) divided by current (I)) and knowing the specific resistivity (Q) and length of the second tubular portion (L), the volume of water in the second tubular portion 104 (V) can be determined.

Having determined the volume of water in the second tubular portion 104 (V), water cut can be determined by determining the volume of the second tubular portion 104 ($V_{tube}$) and subtracting the volume of the water (V) in the second tubular portion 104 from the volume of the tube ($V_{tube}$-V). For example, water cut can be determined as $V/(V_{tube}-V)$.

In some implementations, the current can be continuously flowed through the electrodes in the electrode sub-system 110. Voltage measurements can be taken periodically (for example, several times per second, once per second or once per several seconds). By accumulating voltage measurements over time, impedance over time can be measured and water cut over time can be determined.

Figure 4B:
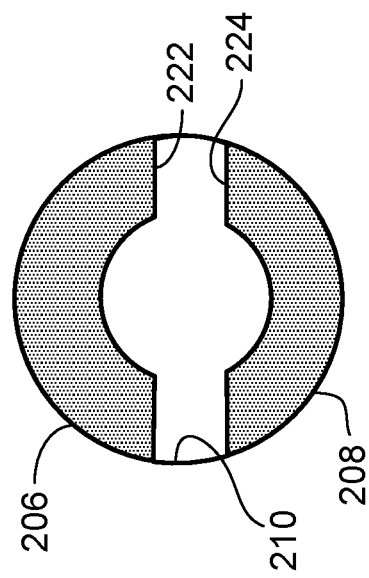

FIGS. 4A and 4B are schematics of a first implementation of an electrode sub-system in the water cut measurement system of FIG. 1. FIG. 4A is a schematic of a side view of the first implementation of the electrode sub-system. The electrode sub-system includes a first electrode 202 and a second electrode 204. Either electrode can be an anode while the other can be a cathode.

The inner surface 212 of the first electrode 202 and the inner surface 214 of the second electrode each has a tapered surface. That is, when viewed from a side, a thickness of each electrode first increases and then decreases along a direction of flow of the multiphase fluid to form a tapered edge (for example, tapered edge 216 of the first electrode 202 and tapered edge 218 of the second electrode 204). The two electrodes can be arranged on the inner wall of the axial portion 114 such that the tapered edges are aligned on a plane 220 that is perpendicular to a longitudinal cross-section of the elongated tubular section 102. In some implementations, the aligned tapered edges can be mid-way along the length of the axial portion 114. The multiphase fluid can converge at this location thereby decreasing a flow path for the current from the first electrode 202 to the second electrode 204.

FIG. 4B is a schematic of a cross-sectional view of the first implementation of the electrode sub-system. In some implementations, each electrode can be sized such that, upon being attached to the inner wall 210 of the second tubular portion 104, the end 222 of the first electrode 202 and the end 224 of the second electrode 202 can be separated by a gap. In some implementations, the two electrodes can be attached to diametrically opposite regions of the inner wall 210 of the axial portion 114. An outer surface 206 of the first electrode 202 and an outer surface 208 of the second electrode 204, each has a shape that is identical to a shape of the inner wall of the axial portion 114. For example, if the inner wall has an arcuate shape, then the outer surface of each electrode has a complementary arcuate shape. Current flows through the axial portion 114.

FIGS. 5A and 5B are schematics of a second implementation of an electrode sub-system in the water cut measurement system of FIG. 1. FIG. 5A is a schematic of a side view of the second implementation of the electrode sub-system. The electrode sub-system includes a first electrode 302 and a second electrode 304. Either electrode can be an anode while the other can be a cathode. The first electrode 302 can be formed as an annular disc. A thickness of the annular disc can be based on the current flowed through the electrode sub-system. The outer surface of the annular disc can contact the inner wall of the axial length 114. The second electrode 304 can be formed as a solid tube positioned concentrically within the first electrode 302.

In some implementations, both implementations of the electrode sub-systems can be implemented in the same flowline. In some implementations, the measurement system including either electrode sub-system can be implemented downhole in a wellbore, at a surface or in a flowline. Implementations of the measurement system described above utilized impedance to flow of alternating current to determine water cut. In some implementations, resistance to flow of direct current can be used to determine water cut. For example, direct current can be flowed through the electrodes. Different components of the multiphase fluid can offer different resistances to the flow of current.

Thus, particular implementations of the subject matter have been described. Other implementations are within the scope of the following claims.

The invention claimed is:

1. A water cut measurement system comprising:
an elongated tubular section configured to flow a multiphase fluid comprising water and hydrocarbons, the elongated tubular section comprising:
a first portion having a first diameter,
a second portion axially coupled to the first portion and having a second diameter less than the first diameter, and
a third portion axially coupled to the second portion and having a third diameter greater than the second diameter; and
an electrode sub-system positioned in the second portion of the elongated tubular section, the electrode sub-system comprising a first electrode and a second electrode configured to flow a current, wherein an outer surface of the first electrode contacts an inner wall of the second portion; and
a controller coupled to the electrode sub-system, the controller configured to determine a ratio of hydrocarbons to water in the multiphase fluid flowed through the elongated tubular section based on an impedance measured by the electrode sub-system responsive to the current flowed through the electrode sub-system.

2. The system of claim 1, wherein each of the first portion, the second portion and the third portion has a circular cross-section.

3. The system of claim 1, wherein the second portion comprises an axial portion that is parallel to a longitudinal axis of the elongated tubular portion, wherein the electrode sub-system is attached to an inner wall of the axial portion.

4. The system of claim 3, wherein the first electrode and the second electrode are attached to diametrically opposite regions of the inner wall of the axial portion.

5. The system of claim 4, wherein the outer surface of each of the first electrode and the second electrode has a shape that is identical to a shape of the inner wall of the axial portion.

6. The system of claim 5, wherein an inner surface of each of the first electrode and the second electrode has a tapered edge.

7. The system of claim 5, wherein a tapered edge of the first electrode and a tapered edge of the second electrode are aligned on a plane perpendicular to a longitudinal cross-section of the elongated tubular section.

8. The system of claim 5, wherein ends of the first electrode and ends of the second electrode are separated by a radial gap.

9. The system of claim 3, wherein the first electrode is formed as an annular disc, wherein an outer surface of the annular disc contacts the inner wall of the axial portion.

10. The system of claim 9, wherein the second electrode is formed as a solid tube positioned concentrically within the annular disc.

11. The system of claim 10, wherein the first electrode is an anode and the second electrode is a cathode.

12. The system of claim 9, wherein a thickness of the annular disc is based on the current flowed through the electrode sub-system.

13. The system of claim 1, wherein the first diameter is equal to the third diameter.

14. The system of claim 1, wherein the second portion comprises:
a first conical tubular portion that couples the first portion to the second portion; and
a second conical tubular portion that couples the third portion to the second portion.

15. A water cut measurement tool comprising:
an elongated tubular section configured to flow a multiphase fluid comprising water and hydrocarbons, the elongated tubular section comprising:
a first portion having a first diameter, and
a second portion axially coupled to the first portion and having a second diameter less than the first diameter, the second portion configured to receive the multiphase fluid from the first portion;
a first electrode attached to an inner wall of the second portion, wherein an outer surface of the first electrode contacts the inner wall of the second portion; and
a second electrode attached to the inner wall of the second portion and positioned diametrically opposite to the first electrode, wherein the first electrode and the second electrode are configured to:
measure an impedance of the multiphase fluid flowed through the second portion responsive to a current flowed from the first electrode to the second electrode, and
provide the impedance as an output.

16. The tool of claim 15, further comprising a third portion axially coupled to the second portion and having a third diameter greater than the second diameter.

17. The tool of claim 15, wherein the second portion comprises an axial portion that is parallel to a longitudinal axis of the elongated tubular portion, wherein the first electrode and the second electrode are attached to an inner wall of the axial portion.

18. The tool of claim 15, wherein the first electrode is formed as an annular disc, wherein an outer surface of the annular disc contacts the inner wall of the second portion, and wherein the second electrode is formed as a solid tube positioned concentrically within the annular disc.

19. The system of claim 7, wherein the aligned tapered edge of each of the first electrode and the second electrode is positioned a distance away from an end of the elongated tubular section.

20. The system of claim 1, wherein the outer surface of each of the first electrode and the second electrode contacts the inner wall of the second portion, resulting in the system configured to operate at a current between 0.1 milliAmpere (mA) and 0.5 milliAmpere (mA).

* * * * *